United States Patent
Lucas

(10) Patent No.: US 11,186,851 B2
(45) Date of Patent: Nov. 30, 2021

(54) CONTINUOUS ETHANOL RECOVERY FROM FERMENTATION WITH HIGH SOLIDS CORN SLURRY PRODUCTION

(71) Applicant: Lucas E3, L.C., Shawnee, KS (US)

(72) Inventor: Scott A. Lucas, De Soto, KS (US)

(73) Assignee: LucasE3, L.C., Shawnee, KS (US)

( * ) Notice: Subject to any disclaimer, the term of this patent is extended or adjusted under 35 U.S.C. 154(b) by 0 days.

(21) Appl. No.: 16/841,254

(22) Filed: Apr. 6, 2020

(65) Prior Publication Data

US 2020/0318145 A1 Oct. 8, 2020

Related U.S. Application Data

(60) Provisional application No. 62/830,076, filed on Apr. 5, 2019.

(51) Int. Cl.
| | |
|---|---|
| *C12P 7/08* | (2006.01) |
| *B01D 5/00* | (2006.01) |
| *B01D 3/00* | (2006.01) |

(52) U.S. Cl.
CPC ............... *C12P 7/08* (2013.01); *B01D 3/004* (2013.01); *B01D 5/006* (2013.01); *B01D 5/0054* (2013.01)

(58) Field of Classification Search
None
See application file for complete search history.

(56) References Cited

U.S. PATENT DOCUMENTS

| | | |
|---|---|---|
| 2,958,142 A | 11/1960 | Kershaw et al. |
| 3,363,340 A | 1/1968 | Mckinley |
| 3,673,705 A | 7/1972 | Wright et al. |
| 4,309,254 A | 1/1982 | Dahlstrom |
| 5,178,543 A | 1/1993 | Semans et al. |
| 5,354,203 A | 10/1994 | Kotch et al. |
| 7,504,546 B2 | 3/2009 | Brown et al. |
| 7,867,365 B2 | 1/2011 | Brown |
| 8,173,412 B2 | 5/2012 | Dale |
| 9,308,489 B2 | 4/2016 | Brown et al. |
| 9,931,582 B2 | 4/2018 | Furlong |
| 10,118,107 B1* | 11/2018 | Kwik .................. C10L 1/02 |
| 2011/0315541 A1 | 12/2011 | Xu |
| 2013/0309738 A1* | 11/2013 | Barr .................. C12M 45/04 435/160 |
| 2014/0238881 A1 | 8/2014 | Stuhlmann et al. |
| 2014/0343259 A1 | 11/2014 | Bleyer et al. |
| 2015/0041305 A1 | 2/2015 | Overheul et al. |
| 2015/0045594 A1 | 2/2015 | Overheul et al. |
| 2016/0279560 A1 | 9/2016 | Furlong |
| 2018/0235167 A1* | 8/2018 | Lewis .................. C12C 12/006 |
| 2018/0290073 A1 | 10/2018 | Brown et al. |
| 2019/0233354 A1 | 8/2019 | Lucas |

OTHER PUBLICATIONS

Katzen, et al., "Ethanol Distillation: the Fundamentals", 1999, 270-273.
Raab, Michael, "Enahnced for Ethanol", Ethanol Producer Magazine, Oct. 2019, ethanolproducer.com/articles/16511/enhanced-for-ethanol, Sep. 16, 2019, 1-2.

* cited by examiner

*Primary Examiner* — Nghi V Nguyen
(74) *Attorney, Agent, or Firm* — Law Office of Mark Brown, LLC; Mark E. Brown

(57) ABSTRACT

A system for continuous ethanol recovery in an ethanol plant includes a prefermenter receiving high solids corn slurry mash from the ethanol plant. A yeast source injects live yeast cells into the prefermenter, which converts sugar in the mash to ethanol and provides beer with a concentration of the ethanol as output. A prefermenter stripper is configured for receiving an outflow airstream and stripping ethanol and water from down-flowing beer. A yeast source injects live yeast cells from the ethanol plant into the prefermenter. The prefermenter converts sugar in the mash to ethanol and provides beer with a concentration of the ethanol as prefermenter output. The prefermenter stripper receives an upflowing airstream and strips ethanol and water from downflowing beer and leaves the top of the prefermenter stripper with ethanol-laden exhaust. A beer recirculation cooler cools the stripped beer using cooling tower water from the existing plant as a heat sink. A continuous ethanol recovery method includes live yeast cell injection, sugar conversion and ethanol and water stripping steps.

9 Claims, 2 Drawing Sheets

CONTINUOUS ETHANOL RECOVERY FROM FERMENTATION WITH HIGH SOLIDS CORN SLURRY PRODUCTION

CROSS-REFERENCE TO RELATED APPLICATION

This application claims priority in U.S. Provisional Patent Application No. 62/830,076, filed Apr. 5, 2019, which is incorporated herein by reference.

BACKGROUND OF THE INVENTION

1. Field of the Invention

The present invention provides systems and methods for continuous ethanol recovery from fermentation with high solids corn slurry production in or in conjunction with an ethanol plant.

2. Description of the Related Art

In efforts to reduce dependence on fossil fuels, alternative fuels, such as ethanol, have been widely promoted. Ethanol is an attractive alternative because its combustion tends to produce more energy with less greenhouse gas emission than fossil fuels. Also, producing ethanol has a positive net energy balance. Reducing or eliminating dependence on fossil fuel imports tends to produce important geopolitical, environmental and global economic benefits at a national level.

Ethanol can be produced by fermenting and distilling starches, e.g., from grains, cellulosic material and other organic matter. The resulting ethanol (alcohol) can be suitable for combustion as a fuel source or a fuel supplement. Grain processing generally produces distiller's grain (DG), including remaining fats, proteins, fiber, oils and minerals. DG can be useful for feeding livestock and other applications.

Energy efficiency is an objective of ethanol production for purposes of reducing distillers' operating costs and the negative environmental effects of their operations. Producing marketable, high-value DG byproducts is another important objective. For minimizing transportation costs, ethanol plants tend to be located near the grain supply sources and the livestock facilities where the DG byproducts are consumed. For example, such plants are relatively common throughout the corn-producing regions of the United States.

The present invention addresses such ethanol distillation plant efficiency objectives by providing a method and system for continuous ethanol recovery from fermentation with high solids corn slurry production in connection with an ethanol plant, with the advantages and features of the present invention.

SUMMARY OF THE INVENTION

In practicing an aspect of the present invention, mash from an existing ethanol plant consisting of high solids corn slurry is fed into one or more prefermenters wherein the mash reacts with live yeast cells from the plant. Sugar in the mash is converted to ethanol resulting in a beer from the prefermenters including an ethanol concentration. The beer is continuously contacted with enough flowing, clean air stream in the prefermenter stripper wherein the feed air stream strips ethanol water off of the down flowing beer, leaving the top of the prefermenter stripper with ethanol-laden exhaust. A beer recirculation cooler cools the stripped beer using cooling tower water from the existing plant as the heat sink. In the practice of the method of the present invention, ethanol is continuously recovered from fermentation with high solids corn slurry production.

BRIEF DESCRIPTION OF THE DRAWINGS

The drawings constitute a part of this specification and include exemplary embodiments of the present invention illustrating various objects and features thereof.

DETAILED DESCRIPTION OF THE PREFERRED EMBODIMENTS

I. Introduction and Environment

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. Said terminology will include the words specifically mentioned, derivatives thereof and words of similar meaning.

Figure 1:
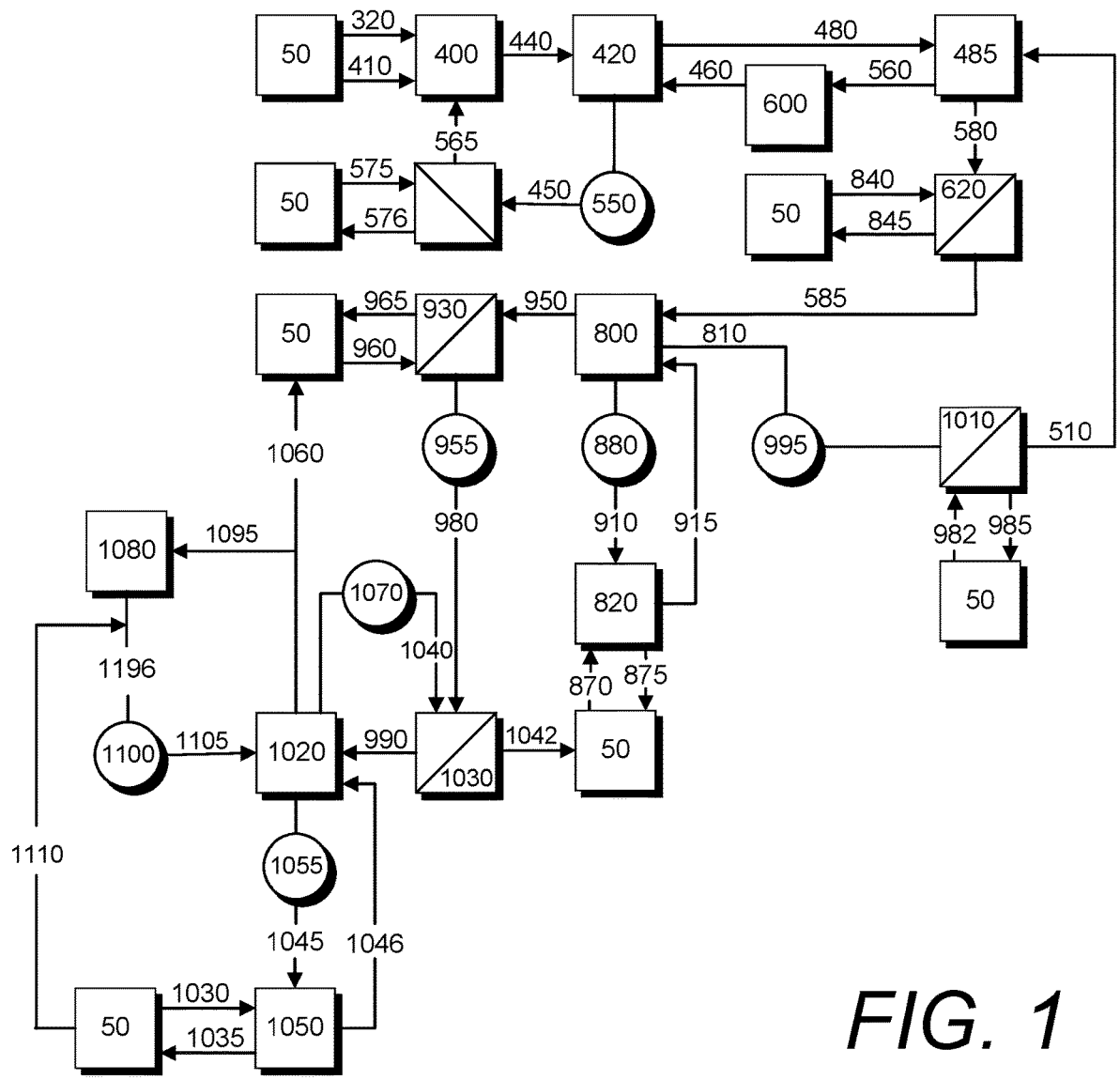
FIG. 1 is a schematic representation of a system for continuous ethanol recovery from fermentation with high solids corn slurry production embodying an aspect of the present invention.

II. Preferred Embodiment Continuous Ethanol Recovery from Fermentation with High Solids Corn Slurry Production As shown in FIG. 1, mash 320 from the existing plant 50, consisting of 40-52% wt solids corn flour slurry at approximately 90° F., is fed to one or more prefermenters 400. Live yeast cells 410 from the existing plant 50 are periodically injected into the prefermenter 400. The yeast 410 reacts with the mash 320, converting the sugar in the mash 320 to ethanol, resulting in a beer 440 from the prefermenter 400 at a concentration of 6-8% wt ethanol.

The beer 440 is continuously contacted with an upflowing, clean 90° F. air stream 460 in the prefermenter stripper 420 where the feed air stream 460 strips ethanol and water off of the downflowing beer 440, leaving the top of the prefermenter stripper 420 as an ethanol laden exhaust 480. The stripped beer 450 at approximately 5-7% wt and 90° F. is returned to the prefermenter 400 using the beer recirculation pump 550 that pumps the stripped beer 450 through a beer recirculation cooler 555, which cools the stripped beer producing an 84° F. return beer stream 565 using cooling tower water 575, 576 from the existing plant 50 as the heat sink.

The ethanol laden exhaust 480 is diverted to the bottom of the ethanol scrubber 485, which receives an 80° F. water stream 510 at the top. The downflowing water stream 510 contacts the upflowing ethanol laden exhaust 480, transferring the ethanol from the exhaust stream to the water stream and producing an ethanol laden water stream 580, which is between 1.0% wt and 4% wt ethanol.

The ethanol-laden exhaust 480 leaves the top of the ethanol scrubber 485 as a clean low-pressure air stream 560, which is fed back to the bottom of the prefermenter stripper 420 using a booster fan 600 to increase the pressure of the stream producing the feed air stream 460. The ethanol laden water stream 580 is preheated in the scrubber bottoms preheater 620 from approximately 100° F. to approximately 130° F. A scrubber bottoms stream 585 is heated using a hot water stream 840 from the existing plant 50 that is approximately 140° F. and cools to approximately 110° F. before being fed back to the existing plant 50 as a return hot water stream 845.

The heated scrubber bottoms stream 585 is fed to the top of the scrubber bottom stripper 800 and is heated using a bottom stripper reboiler 820 receiving a stripper bottoms stream 910 from the scrubber bottom stripper 800, which has been supplied by the scrubber bottom recirculation pump 880. The stripper bottoms stream 910 is heated and partially vaporized in the bottom stripper reboiler 820, creating a partially vaporized stream 915, and is returned back to the bottom of the scrubber bottom stripper 800, providing the heat needed to drive the separation in the stripper. The recirculated stripper bottoms stream 910 is heated by cooling and condensing an existing vapor process stream 870 from the plant 50. The condensed process stream 875 is returned back to the plant 50.

The overhead vapor stream 950, at approximately 20% wt to 40% wt ethanol, is condensed using a vacuum condenser 930, which is cooled using cooling tower water 960 and 965 from the existing plant 50. The condensed overhead steam 980 is pumped to the rectifier column 1020 using the scrubber stripper over condenser pump 955. The clean water stream 810 from the bottom of the scrubber bottom stripper 800 is pumped back to the ethanol scrubber 485 using the scrubber stripper bottoms pump 995. The clean water stream 810 is cooled using ethanol scrubber feed cooler 1010 using cooling water 982 and 985 from the existing plant 50 as the cooling medium. The cooled clean water stream 510 is returned to the ethanol scrubber 485.

The condensed overhead stream 980 from the scrubber bottom stripper 800 is fed to the top of the rectifier column 1020. The feed will be preheated using the condensed overheads preheater 1030, which uses the hot rectifier bottoms 1040 to exchange heat with the condensed overhead stream 980, producing a preheated rectifier feed stream 990. The rectifier column 1020 is heated using a forced recirculation rectifier reboiler 1050, which is heated using steams 1060 and 1035 from the existing plant 50. Rectifier bottoms 1045 are recirculated through the reboiler 1050 using the rectifier reboiler pump 1055, partially vaporizing the stream to produce stream 1046 where this stream is fed back to the bottom of the rectifier column 1020.

Rectifier bottoms 1040 are pumped through the condensed overheads preheater 1030 and back to the existing plant 50 as cooled rectifier bottoms 1042 using the rectifier bottoms pump 1070. The rectifier overheads stream 1060 is split with a portion 1090 fed to the existing plant 50. A portion 1095 is diverted to an existing forced recirculation reboiler 1080 in the existing plant where the vapor stream 1095 is condensed producing a condensed overheads stream 1196 and pumped back to the top of the rectifier column 1020 as rectifier reflux 1105 using the rectifier reflux pump 1100. A liquid ethanol stream 1110 from the existing plant 50 will be mixed with the condensed overheads stream 1196 before being pumped back to the top of the rectifier column 1020.

III. High Solids Corn Slurry Production

Figure 2:
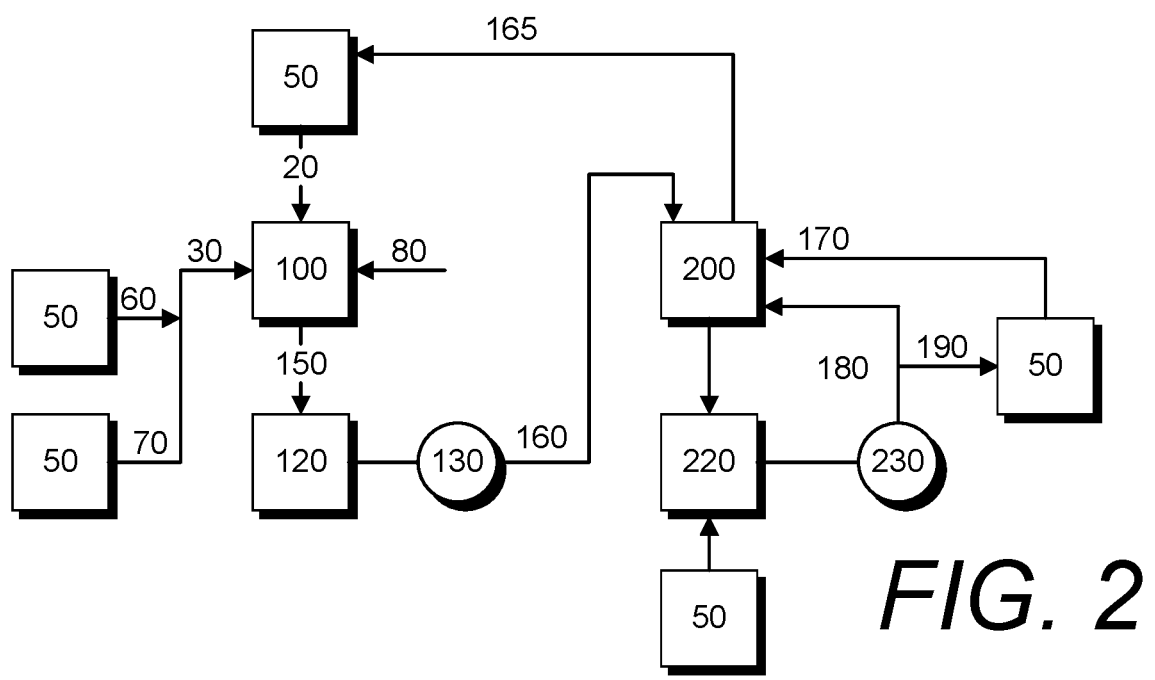
FIG. 2 is a schematic representation of a system for high solids corn slurry production.

As shown in FIG. 2, corn flour 20 from the existing plant 50 is mixed with a cool water stream 30 consisting of recycle water from the existing plant 50. The stream 30 includes treated evaporator condensate 60 and CO2 scrubber bottoms 70 mixed with an alpha amylase enzyme 80 in the slurry blender 100 to produce a slurry 150 consisting of a corn flour water solution at 110° F. to 135° F. and 40% wt to 52% wt. The slurry 150 overflows the slurry blender 100 to the slurry tank 120. From the slurry tank 120 the pumped slurry 160 is fed to the top of the slurry vapor condenser 200 using a first slurry pump 130.

The pumped slurry 160 flows downward, coming into contact with a low-pressure vapor stream 170 from the existing plant 50. Low pressure vapor 170 at approximately 185° F. flows upward through the slurry vapor condenser 200. A portion of the low-pressure vapor 170 is not condensed and leaves the top of the slurry vapor condenser 200 as a vent stream 165. The vent stream 165 is fed back to the existing plant 50 for further processing.

The cool pumped slurry 160 is heated to 180° F. and settles to the bottom of the slurry vapor condenser 200 and into the slurry tank 220. A portion of the heated slurry 180, at approximately 46% wt solids, is recirculated back to the slurry vapor condenser using a second slurry pump 230 and mixes the contents of the slurry vapor condenser 200. High pressure steam 240 from the existing plant 50 heats the slurry tank 220 to 185° F. A portion of the heated slurry 190 is fed back to the existing plant 50 where it is further processed and utilized for ethanol production.

It is to be understood that while certain embodiments and/or aspects of the invention have been shown and described, the invention is not limited thereto and encompasses various other embodiments and aspects.

Having thus described the invention, what is claimed as new and desired to be secured by Letters Patent is:

1. A system for ethanol recovery from high solids corn slurry mash fermentation in an ethanol plant, wherein the system comprises:
    a prefermenter configured for receiving high solids corn slurry mash from the ethanol plant;
    a yeast source configured for injecting live yeast cells from the ethanol plant into the prefermenter;
    said prefermenter configured for converting sugar in the mash to ethanol and providing beer with a concentration of the ethanol as prefermenter output;
    a prefermenter stripper configured for receiving an upflowing airstream and stripping ethanol and water off of downflowing beer;
    a rectifier column receiving a condensed overhead stream from the scrubber bottom stripper;
    a source of live yeast cells configured for injecting said live yeast cells into the mash in said prefermenter;
    a prefermenter stripper with an upflowing clean air stream source configured for stripping ethanol and water off of the downflowing beer and, leaving the top of the prefermenter stripper as an ethanol-laden exhaust;
    a beer recirculation pump configured for returning the stripped beer to the prefermenter through a beer recirculation cooler configured for cooling the stripped beer;
    and a cooling tower in the ethanol plant, said cooling tower configured for providing a source of cooling water and functioning as a heat sink.

2. The system according to claim 1, which includes an ethanol scrubber configured for receiving and ethanol-laden exhaust diverted to a bottom of the ethanol scrubber and receiving a water stream at the top of the ethanol scrubber.

3. The system according to claim 2 configured for feeding ethanol-laden exhaust from the top of the ethanol scrubber as a clean, low-pressure airstream to the bottom of the prefermenter stripper using a booster fan for increasing pressure of the stream producing the feed air stream.

4. The system according to claim 3 configured for splitting the rectifier overheads stream and feeding a portion to the ethanol plant and diverting a portion to an existing forced recirculation reboiler in the existing plan; condensing the vapor stream and producing a condensed overheads stream for pumping to the top of the rectifier column as rectifier reflux; mixing a liquid ethanol stream from the ethanol plant with the condensed overheads stream; and pumping the condensed overheads stream back to the top of the rectifier column.

5. A method of continuously recovering ethanol and producing high solids corn slurry from fermentation, wherein the method comprises the steps of:
   receiving mash with corn flour slurry from an ethanol plant;
   feeding said mash into a prefermenter;
   continuously contacting beer with an upflowing clean air stream in a prefermenter stripper and stripping ethanol and water off of the downflowing beer, leaving the top of the prefermenter stripper as an ethanol-laden exhaust;
   returning the stripped beer to the prefermenter through a beer recirculation cooler;
   cooling the stripped beer with cooling tower water from the ethanol plant as a heat sink;
   diverting ethanol laden exhaust to a bottom of an ethanol scrubber receiving a water stream at the top;
   contacting a downflowing water stream with an upflowing, ethanol-laden exhaust;
   transferring ethanol from the exhaust stream to the water stream and producing an ethanol-laden water stream;
   feeding ethanol-laden exhaust from the top of the ethanol scrubber as a clean, low-pressure airstream to the bottom of the prefermenter stripper using a booster fan for increasing pressure of the stream producing the feed air stream;
   preheating the ethanol-laden water stream in the scrubber bottoms preheater using a hot water stream from the ethanol plant;
   cooling the hot water stream and feeding it back to the ethanol plant;
   feeding the heated scrubber bottoms stream to the top of the scrubber bottoms stripper and heating the heated scrubber bottoms stream with a bottom stripper reboiler supplied by the scrubber bottom recirculation pump; and
   heating and partially vaporizing the stripper bottom stream to create a partially vaporized stream for return to the bottom of the scrubber bottom stripper and provide the heat needed to drive the separation in the stripper.

6. The method according to claim 5, which includes the additional steps of:
   cooling and condensing and existing vapor process stream from the ethanol plant to heat the recirculated stripper bottom stream, and returning the condensed process stream to the ethanol plant;
   condensing the overhead vapor stream and pumping it back to the rectifier column;
   cooling the clean water stream using an ethanol scrubber feed cooler; and
   returning the clean water stream to the ethanol scrubber.

7. The method according to claim 6, which includes the additional steps of:
   feeding the condensed overheads stream from the scrubber bottom stripper to the top of the rectifier column;
   heating the rectifier column using a forced recirculation rectifier reboiler heated using streams from the ethanol plant; and
   recirculating the rectifier bottoms through a reboiler using a rectifier reboiler pump.

8. The method according to claim 7, which includes the additional steps of:
   recirculating the rectifier bottoms through a reboiler using a rectifier reboiler pump, partially vaporizing a stream which is fed back to the bottom of the rectifier column; and
   pumping the rectifier bottoms through condensed overhead preheater's and back to the ethanol plant as cooled rectifier bottoms.

9. The method according to claim 8, which includes the additional steps of:
   splitting the rectifier overheads stream and feeding a portion to the ethanol plant and diverting a portion to an existing forced recirculation reboiler in the existing plan; and
   condensing the vapor stream and producing a condensed overheads stream for pumping to the top of the rectifier column as rectifier reflux; and mixing a liquid ethanol stream from the ethanol plant with the condensed overheads stream; and pumping the condensed overheads stream back to the top of the rectifier column.

* * * * *